United States Patent [19]
Stroda

[11] Patent Number: 6,166,644
[45] Date of Patent: Dec. 26, 2000

[54] PATIENT MONITORING SYSTEM

[75] Inventor: Kristin Robert Stroda, Lincoln, Nebr.

[73] Assignee: Senior Technologies, Inc., Lincoln, Nebr.

[21] Appl. No.: 09/151,020

[22] Filed: Sep. 10, 1998

[51] Int. Cl.[7] .................................. G08B 21/00
[52] U.S. Cl. ............... 340/573.4; 340/521; 340/522; 340/666; 600/595
[58] Field of Search .............. 340/573.4, 573.1, 340/666, 521, 522; 600/595

[56] References Cited

U.S. PATENT DOCUMENTS

| | | | |
|---|---|---|---|
| 4,020,482 | 4/1977 | Feldl | 340/666 |
| 4,160,972 | 7/1979 | La Mell et al. | 340/541 |
| 4,196,425 | 4/1980 | Williams, Jr. et al. | 340/573.4 |
| 4,209,776 | 6/1980 | Frederick | 340/522 |
| 4,263,586 | 4/1981 | Nicholas | 340/573.4 |
| 4,577,185 | 3/1986 | Anderson | 340/573.4 |
| 4,583,084 | 4/1986 | Henderson et al. | 340/573.4 |
| 4,907,845 | 3/1990 | Wood | 340/573.4 |
| 5,494,046 | 2/1996 | Cross | 340/573.4 |
| 5,701,117 | 12/1997 | Platner et al. | 340/522 |
| 5,796,059 | 8/1998 | Boon | 200/85 R |

*Primary Examiner*—Glen Swann
*Attorney, Agent, or Firm*—Vincent L. Carney

[57] ABSTRACT

To monitor a patient, an alligator clip is fastened to the patient by a cord having a length of between five inches and five feet. The other end of the cord is connected to a switch which is activated when the patient moves beyond the length of the cord to cause a message to be announced. A pressure pad is located under the patient and armed by the application of weight to the pad. Upon removal of the weight the alarm is given.

17 Claims, 6 Drawing Sheets

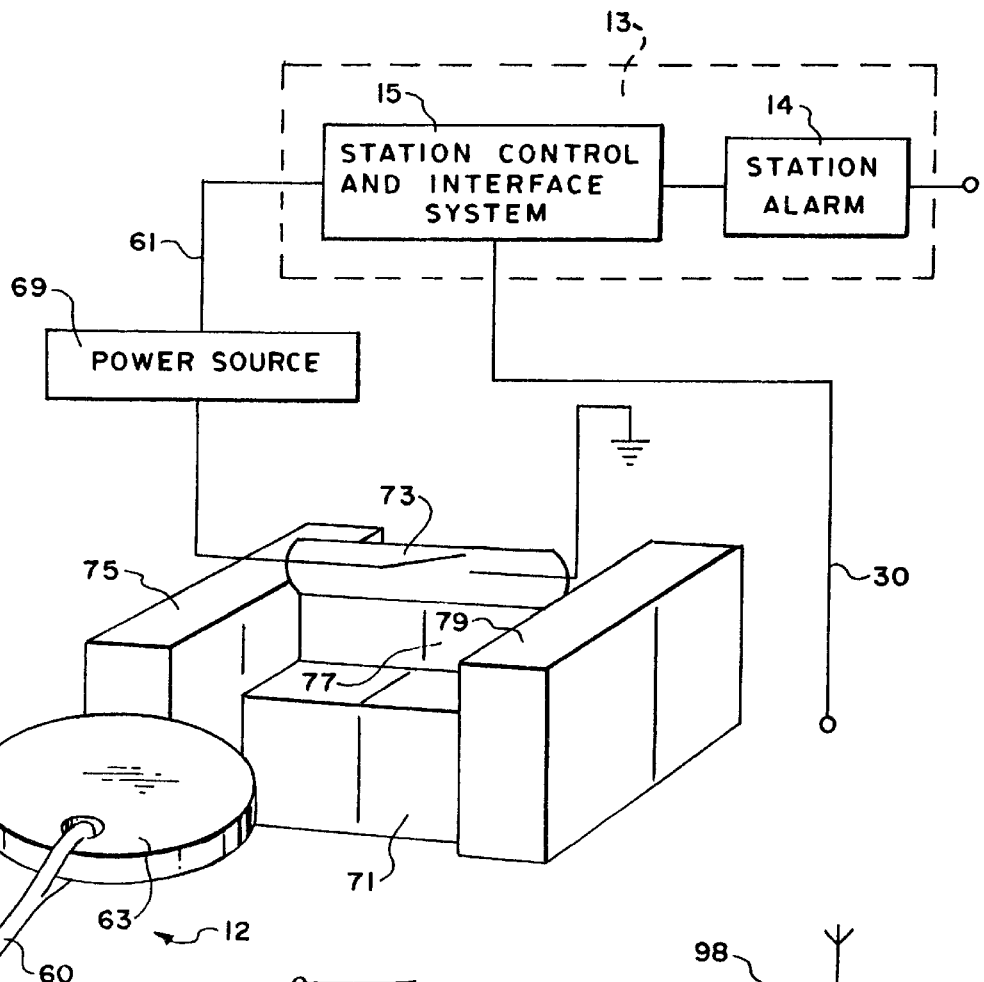
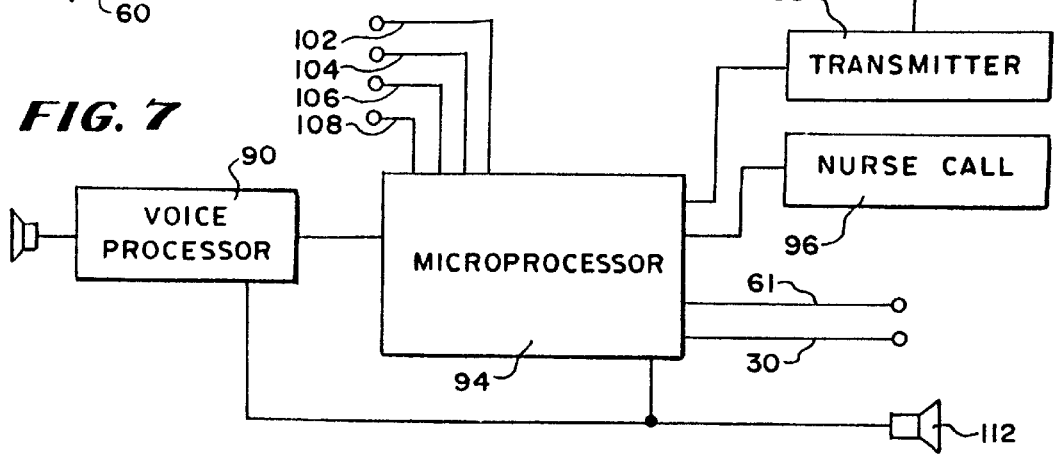

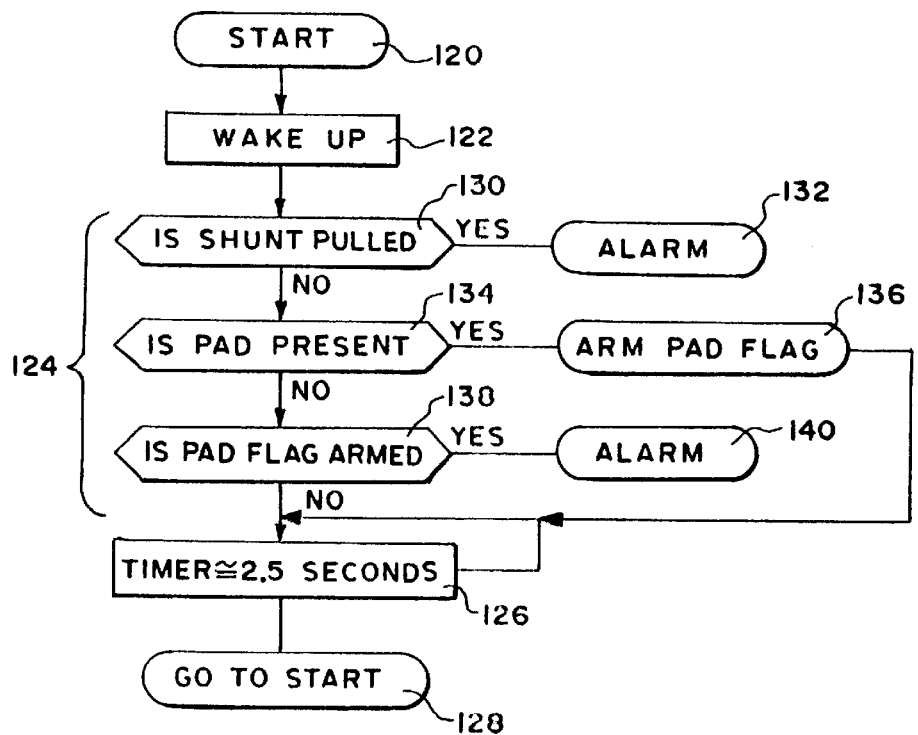
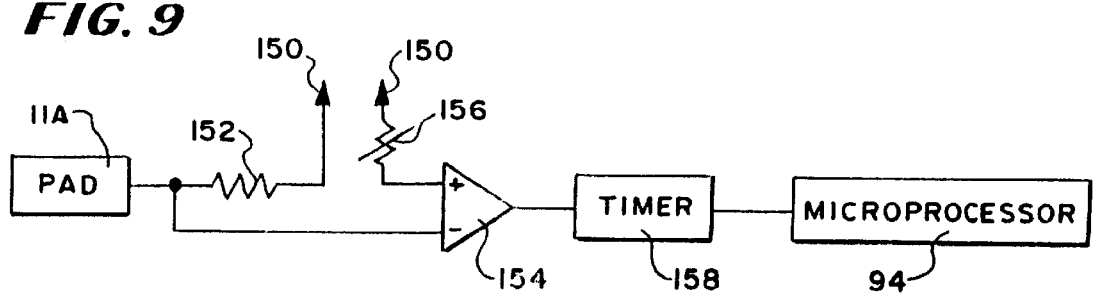

PATIENT MONITORING SYSTEM

BACKGROUND OF THE INVENTION

This invention relates to patient monitoring systems and more particularly to patient monitoring systems in which the movement or location of a patient is determined by any of a plurality of redundant or cooperating sensors and when one or more of the sensors indicates a problem with the patient provides an alarm or a warning.

In one class of patient monitoring systems, a sensor indicates the departure of a patient from his or her expected position and the system responds by providing an alarm. In one such system, a fastener is connected to a monitoring housing by a cord or other device having a fixed length so that if the fastener moves beyond that length, the monitoring housing is activated. The fastener is connected to a patient such as to the clothing of a patient by a clip so that, if the patient moves beyond a fixed distance such as by slumping from a wheelchair onto the floor or moving from a bed, the monitoring housing provides an alarm.

In a prior art monitoring system of this type, the end of the cord opposite to the fastener is loosely fitted into the monitoring housing so that, when the patient moves away from the monitoring housing a distance greater than the length of the cord, that end is pulled free. When the end is pulled free from the monitoring housing, an alarm is given. Prior art systems of this type are disclosed in U.S. Pat. Nos. 4,577,185, 4,858,622, and 4,583,084 and systems of this type are on sale under the trademark, TABS, by Wanderguard, Inc., a division of Senior Technologies, Inc., located at 1620 North 20th Street, P.O. Box 80238, Lincoln, Nebr. 68503.

This type of prior art patient monitoring system has several disadvantages, such as for example: (1) from time to time the fastener falls loose from the patient or is removed by the patient so that the system fails; (2) the patient may become entangled in bedding or the like or fall from the bed or chair or partly fall at a distance that does not pull the cord free; and (3) the cord may break or be cut.

In another class of patient monitoring systems, the patient in a bed or a wheelchair rests on or near a pressure pad. Changes in pressure on that pad cause a signal indicating that the patient is moving in a manner that indicates some type of problem. In a prior art monitoring system of this type, a manual switch is activiated by an attendant or patient when the patient is in place to initiate the monitoring system and inactivated when the patient leaves in an ordinary untroublesome manner. One such prior art system is disclosed in U.S. Pat. No. 4,907,845.

This type of prior art monitoring system has several disadvantages such as for example: (1) the switch may be accidentially thrown or thrown by a patient intending to move but for whom it is undesireable to move unattended because of confusion of the patient or illness to the extent that the patient does not appreciate; (2) because the pressure pad is positioned in the bed beneath the patient, it flexes as the patient moves, causing the cord to flex, eventually fail and thus prevent the signal being given if the patient leaves; and (3) the pad may be defeated by folding or placing a weight on it.

SUMMARY OF THE INVENTION

Accordingly, it is an object of the invention to provide a novel patient monitoring system.

It is a further object of the invention to provide a novel patient monitoring system with at least two sensing modalities that cooperate for increased adaptability and/or reliability.

It is a still further object of the invention to provide a patient monitoring system that is difficult for the patient to defeat either intentionally or accidentally.

It is a still further object of the invention to provide a patient monitoring system in which two or more sensors share the same alarm and signalling equipment.

It is a still further object of the invention to provide a patient monitoring system with increased safety from hazards which inherently can not be detected by a single sensing unit.

It is a still further object of the invention to provide a patient monitoring system which can be set and reset without patient-accessible switches.

It is a still further object of the invention to provide a patient monitoring system including a pressure detecting device which can be set or reset without any manually operated switches.

In accordance with the above and further objects of the invention, a monitoring system, detects when the patient moves inappropriately such as falling from a wheelchair or leaving a bed to which the patient is confined at which includes at least two sensing devices. The sensors back each other up so that if one sensor fails, unauthorized movement by the patient will nonetheless be detected and an alarm sounded. Preferably, the sensors are of two different types such as, for example, one sensing pressure of the patient so that when the patient leaves, the release of pressure gives a signal and another indicating position limits such as a cord so that if the patient moves beyond the cord the system provides an alarm. Other different types of sensors can be motion sensors, temperature sensors or boundary sensors. By using at least two different sensors, errors are reduced because it is less likely that different types of sensors will fail to provide adequate information.

In one embodiment, a first of the sensors is a pressure pad positioned underneath the patient. For example, it may be under the shoulders of a patient that is in bed or on the seat of a wheelchair. When the patient lays against the pad or the chair, a signal is generated which sets the sensor and when weight is removed, an alarm condition is provided.

The second sensor may include a cord fastened at one end to a monitoring housing and at the other end to a clip, such as an alligator clip. The alligator clip fastens the cord to the clothing of a patient at one end of the cord and to an alarm housing at the other end of the cord. When the patient moves beyond the length of the cord such as by falling or the like, a switch changes condition either from an open position to a closed position or a closed position to an open position and the monitoring system issues an alarm.

Other combinations of sensors may include any two or more of several sensors such as for example: (1) motion sensors; (2) light beams that indicate the patient is moving beyond the parimeter of a bed or a wheelchair; or (3) pressure pads that give an alarm signal when pressure is applied. This type of pressure pad is positioned around the rim of the bed indicating that a patient has swung his or her legs over the edge of the bed or along the floor indicating a patient is leaving the bed or connected to supports that a patient may use to pull his or herself out of the wheelchair or the bed and adjusted to the patient's approximate weight as a threshold.

Combinations of these sensors may be selected to accommodate the particular problem. For example, different types of alarms may be associated with different types of switches so that if the patient pulls a cord free indicating that the patient has moved beyond a fixed distance, a voice message may request the patient to remain stationary and a pressure pad around the bed may indicate a different alarm indicating that the patient has left the bed. A longer cord may indicate the patient has fallen or the pressure pad which is triggered upon the release of pressure may quickly provide voice instructions to remain stationary and one alarm whereas the pulling of the cord which is more likely to indicate that the patient has already fallen may give a different distinctive alarm. The voice instructions to the patient to remain stationary may also inform him that an attendant is on the way.

The alarm may be located in the vicinity of the patient or at a remote location or both and may be a lamp, a warning sound and/or a recorded message delivered to the patient. If there is an alarm at the patient's location, it will preferably sound just before a voice message to the patient but in some embodiments, the voice message may play simultaneously with or before the alarm. The voice message may be to soothe the patient and/or to provide instructions such as for the patient to remain stationary until an attendant appears.

The patient monitoring system of this invention has several advantages, such as for example: (1) it provides redundancy so that if one alarm fails the other may succeed to provide a warning alarm; (2) it permits the selection of one or more sensing conditions and combinations of different types of sensors such as one that locates the distance that the patient has moved and another that indicates that the patient has lifted himself or herself off of a pressure pad or has swung his or her legs over the edge of a bed or applied a substantial amount of his or her weight to a support for lifting his or herself from a bed or wheelchair; (3) it can detect distress conditions that might otherwise be missed such as for example a cord indicating a patient is leaving the bed or wheelchair or has fallen from it and a release-of-pressure sensor that indicates the patient may be thrashing about within the length of the cord or dangling from the bed or chair without exceeding the length of the cord; (4) it is difficult for the patient to defeat; and (5) it is relatively flexible in the condition or conditions to be sensed and the nature of the alarm or alarms, or the warnings or messages to the patient, or the sequence of the alarms and messages and the location or locations of the alarm with respect to the caretaker of the patient.

SUMMARY OF THE DRAWINGS

The above noted and other features of the invention will be better understood from the following detailed description when considered in connection with the accompanying drawings, in which:

FIG. 6 is a simplified partly perspective and partly schematic view of a portion of the embodiment of FIG. 1;

FIG. 7 is a block diagram of the control system for an embodiment of the invention;

FIG. 8 is a flow diagram of the program for determining an alarm condition using a pressure pad; and FIG. 9 is a schematic block diagram of a threshold circuit for the pressure pad.

DETAILED DESCRIPTION

Figure 1:
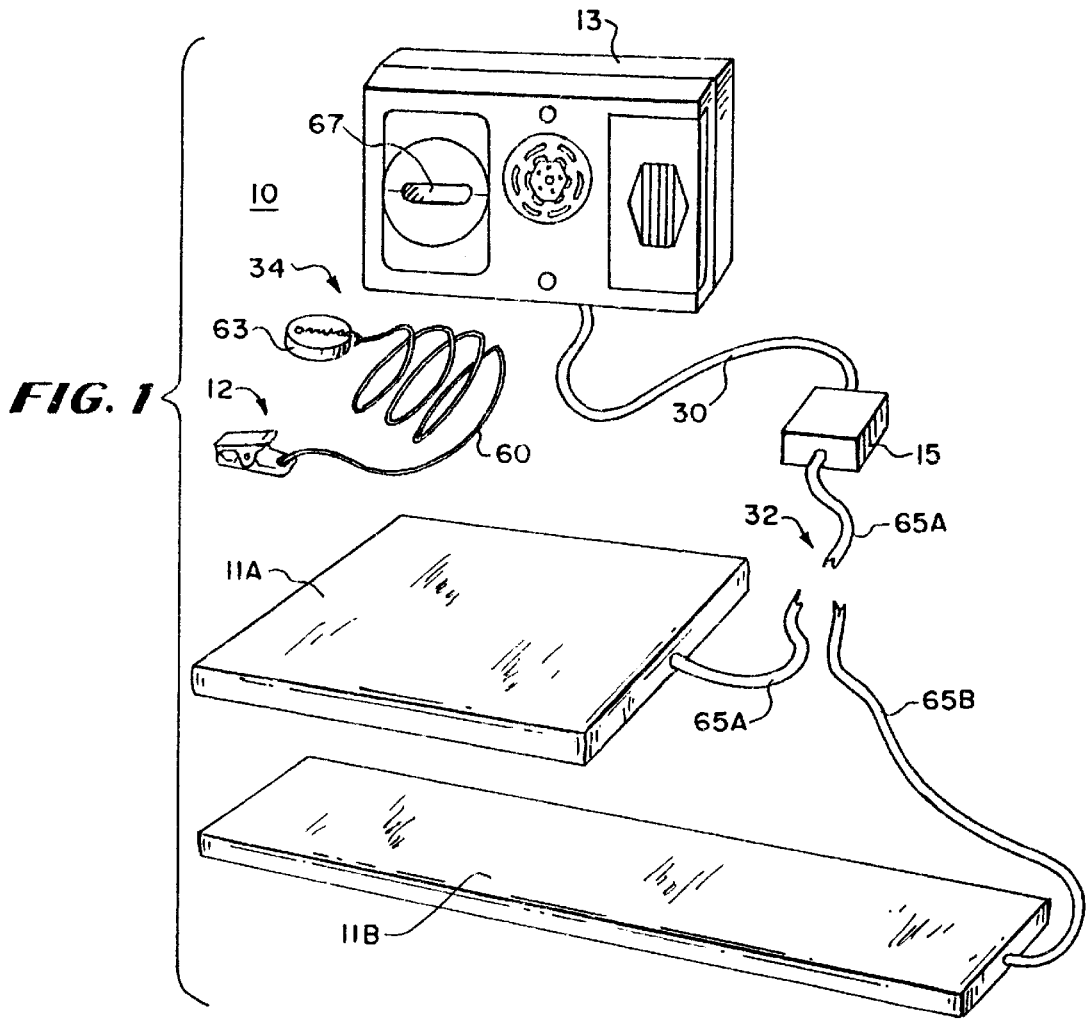
FIG. 1 is a simplified perspective view of an embodiment of the invention.

In FIG. 1, there is shown a simplified perspective view of a patient monitoring system 10 having a wheelchair pressure pad switch 11A a bed pressure pad switch 11B, a cord 60 and a housing 13. A microprocessor (not show in FIG. 1) within the housing 13 is electrically connected to either one of the wheelchair or bed pad pressure switches 11A and 11B (first sensor) to cooperate with them and receive a signal when pressure is applied to the pads or released from the pads. The cord switch 34 (second sensor) includes an alligator clip 12, a cord 60 and a magnetic shunt 63 adapted to fit into a slot 67 in the housing 13. The alligator clip 12 is on one end of the cord 60 and the shunt 63 on the other.

The alligator clip or other connector 12 is fastened to the clothing of the patient and the disk 63 put into the slot 67. When it is removed such as by the person moving a distance greater than that of the cord 60, an alarm and/or voice is sounded. Similarily, when pressure is placed on either the pad 11A in a wheelchair embodiment or the pad 11B in a bed near the shoulders of a patient, a flag on the microprocessor is set so that when the patient releases the pressure such as by getting up from the seat of the wheelchair or sitting up if on a bed, the microprocessor receives a signal resulting in an alarm or voice message and alarm.

To establish the electrical connections between the pressure pads and microprocessor or to pulse forming equipment or threshold equipment for processing signals for input to the microprocessor within the housing 13, the pressure pad 11A is connected by an electrical conductor 65A to the conductor 30 and the bed pressure pad switch 11B is connected by a conductor 65B to conductor 30 with the conductor 65A being shown connected to the conductor in FIG. 1. The input circuits for the microprocessor may be incorporated within the housing 13 and its role is to develop a signal for the microprocessor when pressure is applied on the pressure pads 11A and 11B, which in the preferred embodiment is a pad that reduces resistance when pressure is placed upon it. Other types of pressure pads are known in the art and any of them may be used but some of them would not require the input circuit 15 but would generate their own signal.

In the preferred embodiment, the pressure pads are described in U.S. Pat. No. 5,796,059 to Stephen Boon which are manufactured and available from MicroTech Medical, Inc., 17 Rose Avenue, West Hartford, Conn. 06110 but other types are known such as those disclosed by U.S. Pat. No. 4,263,586 and 4,020,482. The pressure pad described in the aforementioned U.S. Pat. No. 5,796,059 is able to provide signals indicating the location on the pad of pressure and thus, with the aid of the microprocessor detect and indicate shifts in position of the patient such as tilting in a wheelchair or moving to the edge of a bed. While in the preferred embodiment the pressure pad is placed under the bedding it can be placed at other locations such as under the mattress. Moreover, it may be used with an analyzer such as a microprocessor to detect direction of movement such as whether a patient is moving toward a door or away from a door by detecting directional changes in pressure.

In this specification, a sensor includes any device which senses a position or motion or location of the patient. The term sensor not only includes the device for sensing the position, location, movement or the like of the patient but any error correcting or redundant part of it which indicates a failure condition of the sensor itself.

For example, in U.S. Pat. No. 5,494,046 an alligator clip is disclosed attached to a cord and a magnetic shunt similar to that of the preferred embodiment of this invention. However, the alligator clip is designed so that while it is fastened to the garment of the patient, it in itself has an open circuit but when removed, it has a closed circuit so that if this particular sensor has been removed from the patient and is thus disabled to not detect if the patient moves beyond the length of the cord from the housing 13, a signal nonetheless will be provided. However, in this specification it is considered one sensor because it indicates the length of the patient from the housing 13 or the failure of the sensor to be able to detect such a position of the patient.

Figure 2:
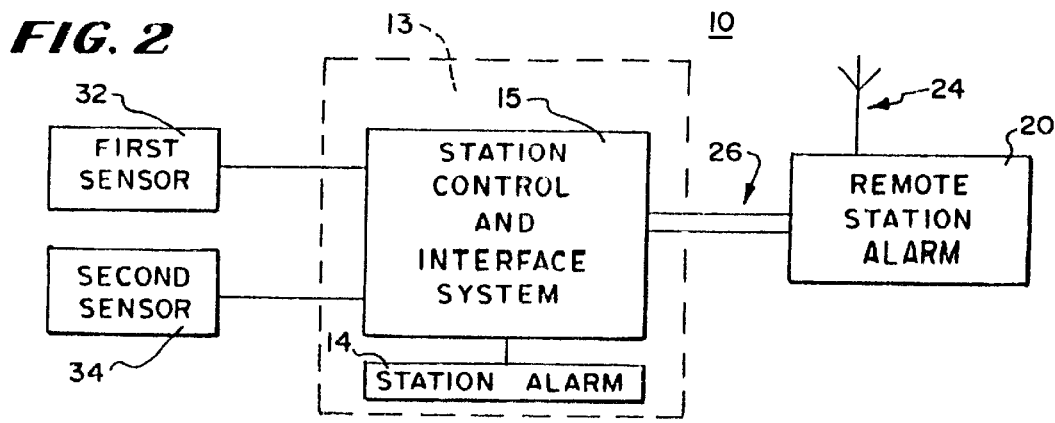
FIG. 2 is a block diagram of a patient monitoring system in accordance with the invention.

In FIG. 2, there is shown a block diagram of a patient monitoring system 10 having a first sensor 32, a second sensor 34, the patient-station monitoring housing 13, a station alarm system 14, a station control and interface system 15, and a remote station alarm 20. The patient-station monitoring housing 13 may include a voice record system in the manner disclosed in U.S. Pat. No. 5,494,046 for providing verbal instructions to a patient under certain sensed conditions. As in the case of the system described in U.S. Pat. No. 5,494,046, the disclosure of which is incorporated herein for reference, an alarm is given at the station with the patient and/or a nurses station before a voice carries a message to the patient so that immediately upon the sensing of an alarm condition, the attendants receive notification and can proceed to the aid of the patient.

In the preferred embodiment, the second sensor 34 is an alligator clip attached to a cord which moves an object in juxtaposition with the housing 13 such as a magnetic shunt that can be removed or a magnet that activates a reed switch, either placed inside or outside of the station alarm unit 14 and the housing 13 or any other type of sensor, many of which are described in U.S. Pat. No. 4,494,046 such as photocell sensors that senses the removal of an object from the housing 13 by uncovering a light path or a mechanical device or any of many sensing devices such that may sense the removal of an object from the interior of the housing 13 or the surface of the housing 13. Because the other sensor develops signals with a different criteria it may be used to reset the pad. For example, the pad sensor may be reset by removing and reinserting the plug 63 into the opening 67 rather than using pressure to both reset after a signal and to arm the sensor.

The station alarm 14 may include a lamp or a buzzer or the like and the remote station 20 may be connected by wires 26 to receive an alarm such as at a remote location such as a nursing station or may have an antenna 24 which receives a signal from the station alarm or transmits a signal to other stations so as to provide an alarm at those stations. The alarms at the remote stations may also be any type of indicator such as a lamp, a buzzing sound, a ringing sound, a horn-like sound, or a voice.

While in the embodiment of FIG. 2, alarms are provided before the message is played both near the patient and at a remote location, the alarm nearby from the station alarm may be omitted and the signal transmitted directly to the remote station or alarm 20 or the message may be played simultaneously with either or both the station alarm 14 and remote alarm 20 or before either or both alarms. The voice system may be any standard commercial arrangement such as are now commonly used to play a fixed message. In the preferred embodiment, the voice system is a single chip, voice record/playback device Model ISD14XX sold under the trademark DAST by Information Storage Devices, Inc., 2841 Junction Avenue, Suite 204, San Jose, Calif., 95134.

Figure 3:
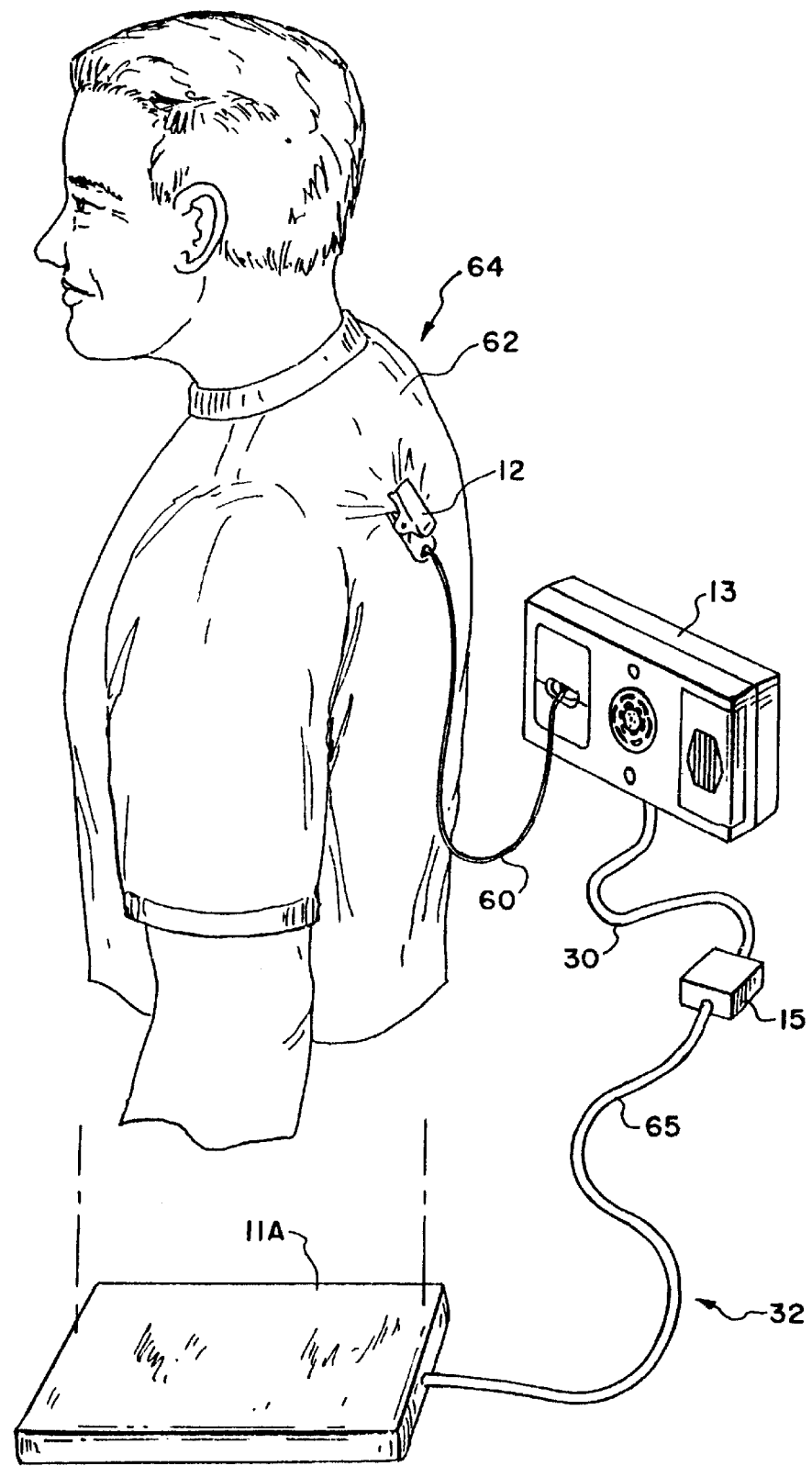
FIG. 3 is a fragmentary, simplified perspective view showing a manner in which the fastener, a cord and pressure pad are used to monitor a patient.

In FIG. 3, there is shown a fragmentary, simplified perspective view of a patient 64 wearing a garment 62 and having the alligator clip or other fastener 12 fastened to the garment 62 and connected by at least one length of cord 60 to the housing 13 at the patient station constituting the second sensor which is a cord switch 34 in the embodiment of FIG. 1 and a pressure pad 11A and switch 15 constituting a first sensor 32. In the preferred embodiment, the alligator clip 12 is fastened by a first length of cord 60 to a switch member (not shown in FIG. 3) that may be pulled from its position in the housing 13 to signal an alarm easier than the alligator clip or other fastener 12 is freed from the garment 62. The pressure pad 11A is intended to be on the seat of a wheelchair to provide a signal if the patient leaves the wheelchair.

The length of cord 60 should be selected for the use but should be within a range of five inches to five feet and preferably within a range of ten inches to twenty inches for a chair and still more preferably 15 inches for a chair. It should be preferably within a range of two feet to three feet for a bed and still more preferably thirty inches.

The alarm switch may be of any type, such as for example the switch disclosed in U.S. Pat. No. 4,160,972, the disclosure of which is incorporated herein by reference when used to activate an alarm when the switch is opened. To activate an alarm when a switch is closed rather than when opened, a source of power in series with the alarm and switch may be used. Moreover, a voice processor 90 (FIG. 7) within the housing 13 may be used with other types of systems such as that disclosed in U.S. Pat. No. 4,577,185, the disclosure of which is incorporated by reference herein, to activate an alarm when the length of cord 60 is pulled free from the housing. Thus, the cord 60 may pull a ferromagnetic member away from a reed switch or may pull a mechanical switch closed or open or may move an opaque object from or into a location between a light source and a photocell to change the state of a switch and thus activate a voice recording and one or more alarms. The alarms 14 and 20 (FIG. 2) may be audible or visual or both.

With this arrangement, if the patient were to move further away from the housing 13 such as by falling from a chair or leaving a bed, the cord 60 would stretch and pull the magnetic shunt 63 (FIG. 1) or other member, free from the slot 67 (FIG. 1), closing a circuit in the housing 13 to activate the alarm and/or voice recording. Moreover, if pressure were released on the pads 11A or 11B a signal would be given to provide an alarm.

The alligator clip or other fastener 12 is generally fastened to the torso of a patient such as on a shirt or the top part of a hospital gown or the like in the vicinity of the shoulder and the cord 60 is sized in accordance with the location of the monitoring apparatus. For example, in a wheelchair, the cord 60 is generally 18 inches long and in a bed setting it is generally two feet long. It should be no shorter than one foot and no longer than five feet in length. The housing 13 is generally fastened to a nearby support.

Figure 4:
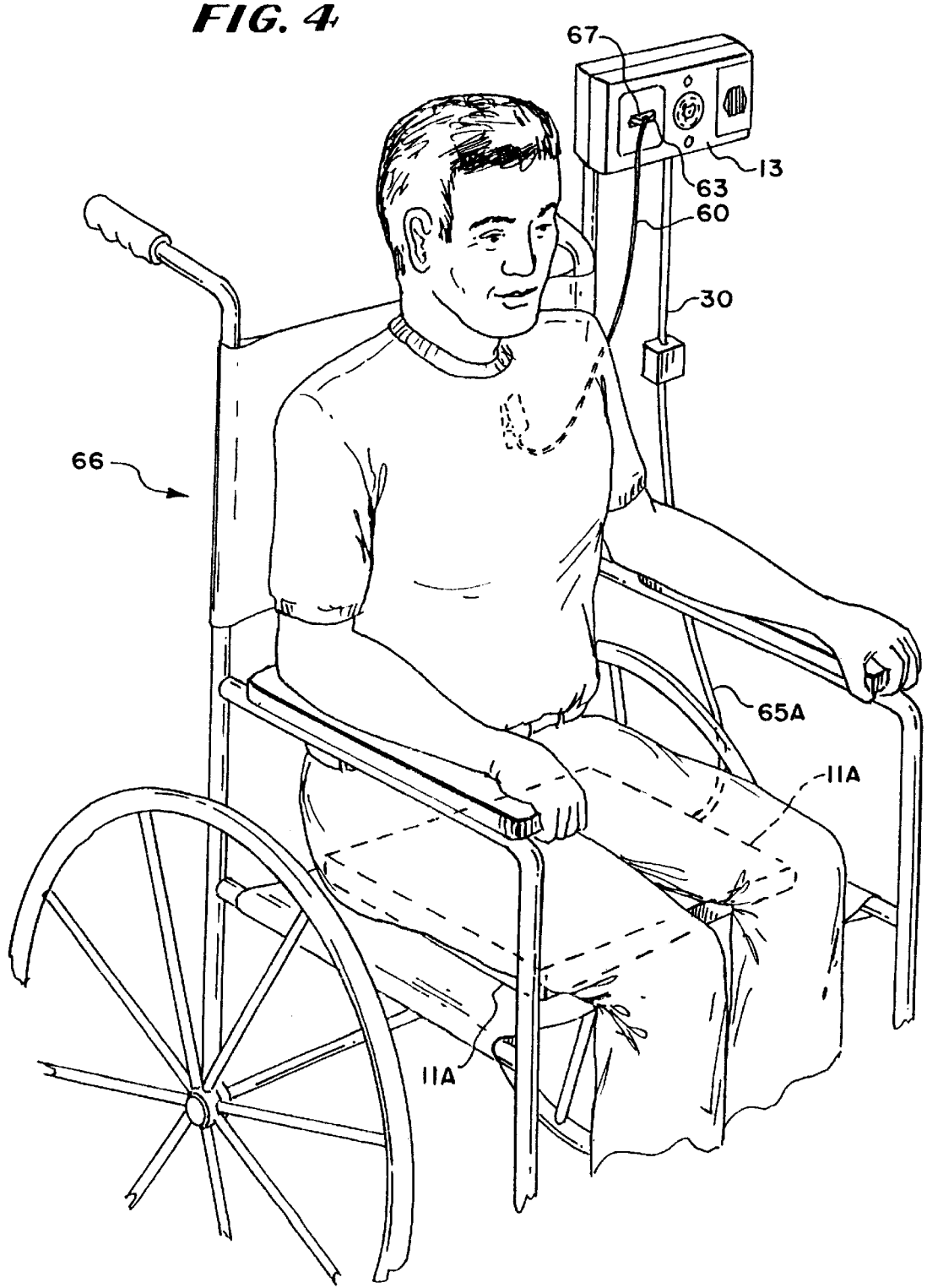
FIG. 4 is a fragmentary simplified perspective view illustrating the use of the patient monitoring system in connection with a wheelchair.

In FIG. 4, there is shown a fragmentary, simplified perspective view of a wheelchair 66 showing an appropriate mounting for the housing 13 above the wheelchair with the cord 60 facing forwardly and being connected to the alligator clip and magnetic disk 63 in the slot 67 of the housing 13 so that a patient in the wheelchair may have the clip 12 fastened to the patient's garment. The pressure pad 11A is under the patient's seat so that the patient's weight is upon it. In the preferred embodiment, the cord is fifteen inches long. If the patient then slumps forward out of the chair, the disk 63 is pulled free from the slot 67 or pressure released on the pressure pad 11A, the housing 13 provides an alarm signal to a caretaker, preferably at a remote location. The recorded message in an embodiment of this type may request the patient to remain stationary until aid arrives.

Figure 5:
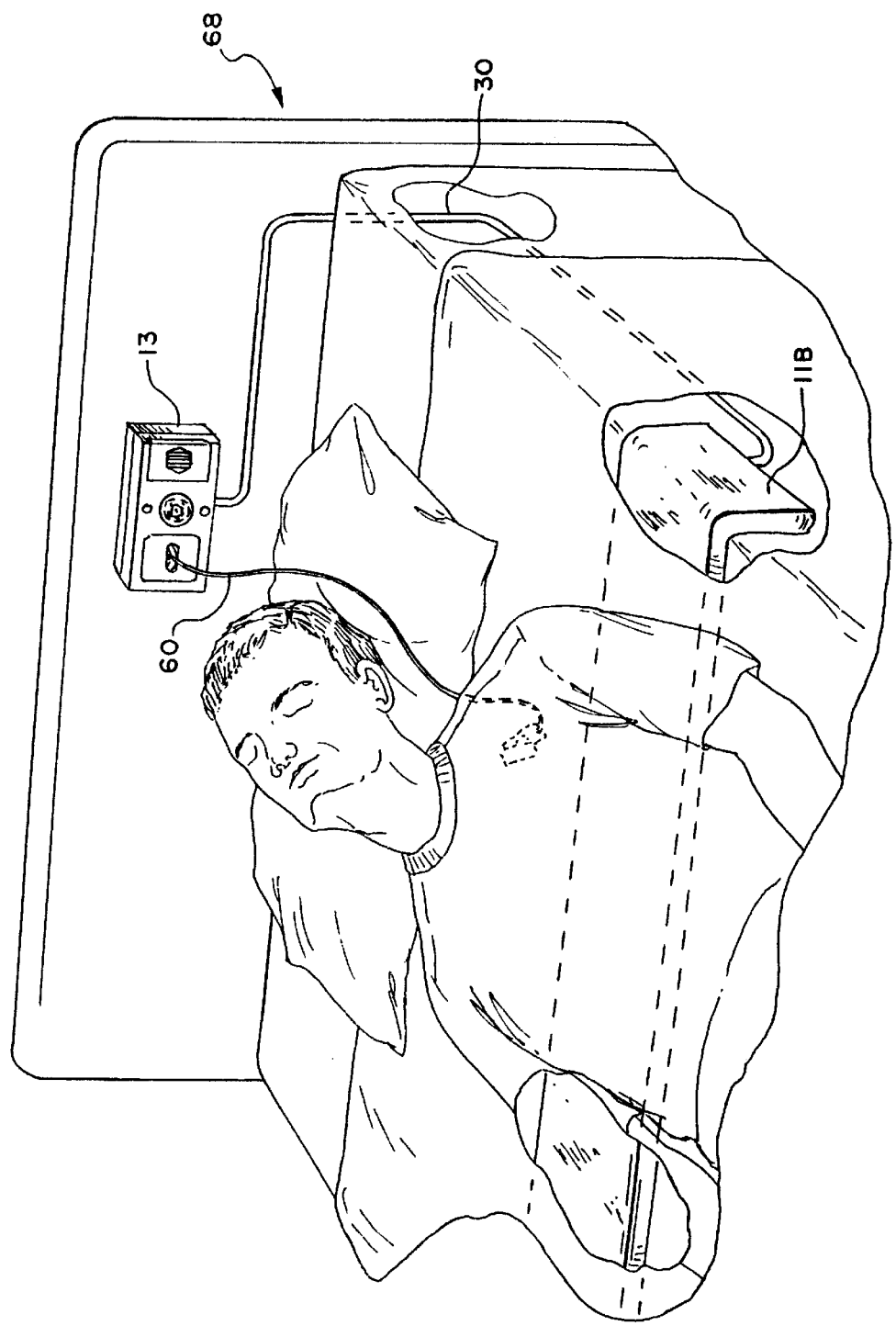
FIG. 5 is a simplified, perspective, fragmentary view illustrating the use of the patient monitoring system in connection with a bed.

In FIG. 5, there is shown a simplified, perspective, fragmentary view of a bed 68 equipped with a patient's station monitoring housing 13 mounted to the headboard so that the alligator clip 12 (FIGS. 1 and 3) can be fastened to a patient. The cord 60 has a length so that if the patient falls from the bed or attempts to leave, the cord 60 will cause either the disk 63 (FIGS. 1 and 4) to be pulled from the housing 13 or the pressure pad 11B receive less weight and generate a signal. The pressure pad is under the shoulders of the patient. In either case, a message may be played requesting the patient to remain in the bed and/or an alarm may be transmitted to a caretaker who can attend to the matter. In the preferred embodiment, the cord is 30 inches long.

In FIG. 6, there is shown a simplified, fragmentary, partly-perspective and partly-schematic view of one possible embodiment of the patient monitoring system 10 having the first length of the cord 60, the station alarm 14, the pressure pad sensor conductor 30 connected so that when the magnetic shunt 63 is pulled free from the housing 13, the reed relay 73 closes about the power supply 69 to send a signal through the conductor 61 to the station control and interface system 15 to provide an alarm signal and when the weight on one of the pressure pads is released, a signal is sent through conductor 30 through the station control and interface system 15 to provide an alarm. The station control and interface system 15 performs the "OR" function within the microprocessor 94 (FIG. 7) or by a separate "OR" gate before the microprocessor.

In the embodiment of FIG. 6, the housing includes a permanent magnet or an energized electrode magnet 71, a reed relay 73, and ferromagnetic path members 75, 77 and 79. The ferromagnetic path members 75, 77 and 79 form a closed ferromagnetic circuit with the magnet 71. This ferromagnetic circuit maintains the normally open reed relay 73 in its open position. The magnetic shunt 63 is ferromagnetic, and when seated so that it rests on the members 75 and 79, forms a ferromagnetic shunt that diverts flux away from the member 77, thus permitting the reed relay 73 to close.

With this arrangement, when the disk 63 is pulled free, a signal is transmitted to the station control and interface system 15 and the station alarm 14 to initiate the voice message and/or alarm from the voice processor 90 (FIG. 7) of the housing 13 (FIGS. 1, 3, 4 and 5) and the remote station alarm 20 (FIG. 2) as explained in connection with FIG. 2.

FIG. 7 is a block diagram of the control system for an embodiment of the invention and has its principle parts a microprocessor 94, a transmitter 98, an alarm speaker 112, a nurse call 96 and a voice microprocessor 90. The microprocessor 94 is a type PIC16C54 Microcontroller sold by Microchip Technology, Inc. of Arizona. It's an 18-pin microprocessor having an input 102 for tone select, an input 104 for another tone select, an input 106 for local alert and 108 for local voice to set the microprocessor 94.

With this arrangement, when an input signal is received from the conductor 30, a flag is set in the microprocessor 94. When a signal is received indicating a release of the pressure, the microprocessor 94 transmits an alarm signal to the nurse call station 96, the transmitter 98 and the alarm speaker 112 within two and one-half seconds unless the pressure is again applied to the sensing pad. If set for that purpose, a signal may be sent to the voice microprocessor 90. This provides the warning to the patient. similarly, a signal from the station control and interface system 15 (FIG. 6) or similar component in other circuit arrangement from other sensors indicating that the first sensor which is the magnetic shunt 63 has been pulled free, initiates an alarm signal.

In FIG. 8, there is shown a flow diagram of a program utilizable in the microprocessor 94 (FIG. 7) to determine an alarm condition using a pressure pad which program includes a start step 120, a wake-up or power starting and initializing step 122, an alarm condition detecting step 124, a timer step 126 and a go to start step 128. With this arrangement, the microprocessor 94 (FIG. 7) is initialized such as at the step 122 and determines if there is an alarm condition caused by the shunt being removed or the pressure pad being armed and removed, determines if there is an alarm condition on the pad if it lasts for approximately 2.5 seconds and returns to start step 128.

The alarm condition detecting step 124 includes the steps of determining if the shunt is pulled at step 130, providing an alarm signal as shown at 132 if it has been pulled, and if it has not been pulled, going to the decision step 134. The decision step 134 determines if the pad is present and if it is, the program proceeds to the arm the pad step 136 by applying a pressure pad flag if pressure has been applied to the pressure pad to reduce resistance. If the pad is not present, then the program proceeds to the decision step 138 to determine if there is an armed pad flag, and if there is, then it proceeds to the step 140 to provide an alarm. If not, it proceeds to the timer step 126 and from there back to the start step 120 from the go to start step 128. If the armed pad flag 136 is set as a result of the pad being present and weight being upon it then the program proceeds to the timer step 126 and from there back through steps 120, 122, 130, 134, 138 and alarm step 140.

With this arrangement, an alarm is provided if the shunt is pulled or if the flag is armed and weight is removed for approximately 2.5 seconds.

In FIG. 9, there is shown a schematic block diagram of the microprocessor circuitry 94 connected to the pad 11A. The pad is energized by a source of voltage 150 and applied to the pad 11A through a resistor 152. A comparator 154 has its noninverting input terminal energized by the battery source 150 through an adjustable resistor 156 that determines a threshold value for the pad that can be set to accomodate the weight and size of a person on the pad. The pad provides the signal as determined by 150 and controlled by the resistance of the pad 11A to the inverting terminal of the comparator 154 to initiate a timer 158, which may be within the microprocessor or separate from the microprocessor. If this condition as determined by the comparator 154 lasts for approximately 2.5 seconds then the microprocessor provides an alarm signal. But if the threshold from the pad 11A as applied to the comparator 154 falls at the noninverting input terminal, then the timer 158 is reset and no alarm is given.

The patient monitoring system of this invention has several advantages, such as for example: (1) it provides redundancy so that if one alarm fails the other may succeed to provide a warning alarm; (2) it permits the selection of one or more sensing conditions and combinations of different types of sensors such as one that locates the distance that the patient has moved and another that indicates that the patient has lifted himself or herself off of a pressure pad or has swung his or her legs over the edge of a bed or has applied a substantial amount of his or her weight to a support for lifting his or herself from a bed or wheelchair; (3) it can detect distress conditions that might otherwise be missed such as for example a cord indicating a patient is leaving the bed or wheelchair or has fallen from it and a release-of-pressure sensor that indicates the patient may be thrashing about within the length of the cord or dangling from the bed or chair without exceeding the length of the cord; (4) it is difficult for the patient to defeat; and (5) it is relatively flexible in the conditions to be sensed, the nature of the alarm or alarms or the warnings or messages to be given, the sequence of the alarms and messages and the location or locations of the alarm with respect to the caretaker or the patient are selectable.

Although a preferred embodiment of the invention has been described with some particularity, many modifications and variations of the preferred embodiment are possible within the light of the above teachings. Therefore, it is to be understood that, within the scope of the appended claims, the invention may be practiced other than as specifically described.

What is claimed is:

1. A method of monitoring a patient comprising the steps of:

placing a first and second sensor in juxtaposition with a patient whereby when the patient assumes a dangerous position as indicated by either the first or second sensor an alarm signal is provided, whereby the first sensor is one of a switch activated by a flexible member fastened to a patient, a light beam switch, a motion sensor and a pressure sensor; and the second sensor is a different one of a switch activated by a flexible member fastened to a patient; a light beam switch, a motion sensor and a pressure sensor; and activating a monitoring station when the alarm signal is provided, whereby a voice message is announced in the vicinity of the patient.

2. A method in accordance with claim 1 in which an alarm is provided to a caretaker.

3. A method in accordance with claim 1 in which an alarm is provided in the vicinity of the patient.

4. A method in accordance with claim 1 in which an alarm is provided at a remote station.

5. A method in accordance with claim 1 in which one of said first and second sensors is a pressure pad.

6. A method of monitoring a patient comprising the steps of:

placing a first and second sensor in juxtaposition with a patient whereby when the patient assumes a dangerous position as indicated by either the first or second sensor an alarm signal is given;

activating a monitoring station when the alarm signal is given, whereby a voice message is announced in the vicinity of the patient; and one of the first and second sensors is armed by the application of weight to it.

7. A method of monitoring a patient, comprising the steps of:

attaching a fastening means to a patient, whereby if the patient moves beyond a predetermined distance, a first switch moves between one of an open state or a closed state to the other of the open or closed state whereby an alarm signal is provided;

placing a pressure pad under the patient whereby a second switch moves between one of an open state or a closed state when pressure is put on the pressure pad;

providing an alarm signal when pressure on the second switch is removed to move the second switch to the other of the open state or closed state.

8. A method in accordance with claim 7 in which the step of attaching the fastening means to the patient includes the step of attaching the fastening means to the clothing of the patient.

9. A method in accordance with claim 7 in which the step of providing an alarm signal includes the step of providing a verbal message to the patient.

10. A method in accordance with claim 7 in which the step of providing an alarm signal includes the substeps of transmitting a signal to a remote station and providing an alarm signal to a caretaker at the remote station.

11. Apparatus for monitoring a patient, comprising:

a control housing mounted to a patient station;

a flexible member attached to the control housing, said flexible member including a fastening means on one end for attaching to the patient and a switch on the other end, a pressure pad located so that the pressure pad is under the patient, the control housing including a means for providing an alarm signal when the fastening means or pressure pad is activated.

12. Apparatus for monitoring a patient in accordance with claim 11 in which said pressure pad is activated by removal of pressure and inactivated by application of pressure.

13. Apparatus in accordance with claim 11 in which said fastening means includes a spring means for biasing jaws in a closed position.

14. Apparatus in accordance with claim 11 in which said alarm signal includes a recorded voice message sounding within hearing distance of the patient to which said fastening means has been attached.

15. Apparatus for monitoring a patient having first and second sensors; said first sensor sensing one of the motion, distance, location or weight of the patient and the second sensor sensing a different one of the motion, distance, location or weight of the patient, either said first or second sensors being able to trigger an alarm.

16. A patient monitoring system, comprising:

pressure pad means for responding to pressure by reducing electrical resistance between a first point and a second point; switch means armed upon the reduction of electrical resistance; an alarm means for providing an alarm when the switch means has been armed and electrical resistance is over the predetermined threshold for more than 1 second, whereby the movement of the patient from the pad triggers an alarm.

17. A patient monitoring system according to claims 16 in which the alarm means provides an alarm when the switch means has been armed and electrical resistance is over the predetermined threshold for a time between 2 seconds and 3 seconds in duration.

* * * * *